(12) United States Patent
Valentini

(10) Patent No.: US 9,857,349 B2
(45) Date of Patent: Jan. 2, 2018

(54) DEVICE AND A METHOD FOR PERMEATION HYDROGEN MEASUREMENTS

(71) Applicant: LETOMEC S.R.L., Pisa (IT)

(72) Inventor: Renzo Valentini, Pisa (IT)

(73) Assignee: LETOMEC S.R.L., Pisa (IT)

( * ) Notice: Subject to any disclaimer, the term of this patent is extended or adjusted under 35 U.S.C. 154(b) by 61 days.

(21) Appl. No.: 14/436,467

(22) PCT Filed: Oct. 25, 2013

(86) PCT No.: PCT/IB2013/059675
§ 371 (c)(1),
(2) Date: Apr. 16, 2015

(87) PCT Pub. No.: WO2014/064658
PCT Pub. Date: May 1, 2014

(65) Prior Publication Data
US 2015/0301010 A1    Oct. 22, 2015

(30) Foreign Application Priority Data
Oct. 25, 2012 (IT) ................... PI2012A0109

(51) Int. Cl.
*G01N 33/20* (2006.01)
(52) U.S. Cl.
CPC .................. *G01N 33/203* (2013.01)
(58) Field of Classification Search
CPC .................................................. G01N 33/203
(Continued)

(56) References Cited

U.S. PATENT DOCUMENTS 2,886,497 A * 5/1959 Butler .................. G01N 15/08
                                                           204/400
3,357,903 A * 12/1967 Lawrence, Jr. ........ C25D 21/12
                                                           204/400
(Continued)

FOREIGN PATENT DOCUMENTS

EP        1114992        7/2001
GB        2312279       10/1997
(Continued)

OTHER PUBLICATIONS

PCT International Search Report dated Mar. 3, 2014 for PCT/IB2013/059675 filed on Oct. 25, 2013 in the name of Letomec S.R.L.
(Continued)

*Primary Examiner* — Daniel S Larkin
(74) *Attorney, Agent, or Firm* — Steinfl + Bruno LLP

(57) ABSTRACT

A method and a device for measuring a content of hydrogen absorbed by a metal workpiece by permeation in the form of hydrogen atoms are described. The device includes a probe with a mixing chamber accessible to an amount of hydrogen emanating from the workpiece, and communicating with an inlet port of a measurement gas. The device further includes a solid-state hydrogen concentration sensor pneumatically connected with the mixing chamber, a gas transfer means for forming a flow of a measurement gas from the inlet port to the sensor, and a processor means for processing a concentration signal of the sensor and for producing a parameter related to the interaction between the metal workpiece and the absorbed hydrogen.

6 Claims, 6 Drawing Sheets

(58) Field of Classification Search
USPC .......................................... 73/19.07, 38, 86
See application file for complete search history.

(56) References Cited

U.S. PATENT DOCUMENTS

| | | | |
|---|---|---|---|
| 4,192,175 A | 3/1980 | Godai et al. | |
| 4,907,440 A | 3/1990 | Martin et al. | |
| 6,196,060 B1 * | 3/2001 | Yepez | G01N 33/203 |
| | | | 73/86 |
| 6,537,824 B1 * | 3/2003 | Correa | G01N 17/02 |
| | | | 422/53 |
| 6,637,253 B2 * | 10/2003 | Dean | G01N 1/24 |
| | | | 73/23.2 |
| 7,306,951 B1 * | 12/2007 | Benson | G01N 21/783 |
| | | | 422/83 |
| 2009/0277249 A1 | 11/2009 | Polster et al. | |

FOREIGN PATENT DOCUMENTS

| | | |
|---|---|---|
| WO | 00/75634 | 12/2000 |
| WO | 2011/131897 | 10/2011 |

OTHER PUBLICATIONS

PCT Written Opinion dated Mar. 3, 2014 for PCT/IB2013/059675 filed on Oct. 25, 2013 in the name of Letomec S.R.L.
PCT International Preliminary Report on Patentability dated Jan. 27, 2015 for PCT/IB2013/059675 filed on Oct. 25, 2013 in the name of Letomec S.R.L.

* cited by examiner

DEVICE AND A METHOD FOR PERMEATION HYDROGEN MEASUREMENTS

CROSS REFERENCE TO RELATED APPLICATIONS

The present application is the US national stage of International Patent Application PCT/IB2013/059675 filed internationally on Oct. 25, 2013 which, in turn, claims priority to Italian Patent Application No. PI2012A000109 filed on Oct. 25, 2012.

FIELD OF THE INVENTION

The present invention relates to a device for determining the hydrogen concentration in a mixture with another gas.

The device can be used for determining or following the hydrogen production absorption into metal workpieces during a surface treatment in a chemical or electrochemical bath.

The device can also be used for monitoring corrosion and hydrogen permeation in metal workpieces, such as piping used in corrosive environments or in contact with hydrogen-comprising gases in the petrochemical industry, in power plants or in hydrogen-production/distribution facilities, in particular, in component used at high temperatures.

The device can be further used for carrying out non-destructive tests of welded joints.

The device can be also used for evaluating hydrogen diffusivity in a solid material, in particular in a metal.

BACKGROUND OF THE INVENTION

As well known, hydrogen can reduce the strength of the metal workpieces with which it comes systematically into contact. This is true, in particular, in the case of steels. In fact, a long-lasting contact with hydrogen gas, as it may be the case in some process environments, may cause hydrogen to be absorbed into the metal. Beyond a certain extent, this may give rise to hydrogen embrittlement. For instance, chemical or electrochemical surface treatment processes are known for treating metal workpieces, such as galvanic treatments, pickling, chemical milling or electropolishing. These processes take place by a reduction reaction of the hydrogen that is present as $H^+$ ion in a treatment bath. This way, atomic hydrogen is generated that may remain within the treated workpiece, and may cause embrittlement.

Various procedures are known for assessing the risk of hydrogen embrittlement in an industrial galvanic treatment process. For instance, ASTM F519-10 provides destructive tests on a significant number of specimens that must be prepared according to specific procedures. ASTM F 326-96 provides measuring a hydrogen absorption parameter during the treatment, and measuring its permeability during a subsequent dehydrogenation treatment. These procedures have the drawback of being too costly. Moreover, these are indirect and not well-timed tests. In other words, samples are used that are distinct from the workpieces actually treated, and a certain amount of time must be waited in order for the results of the tests to be available. Therefore, if a result is not acceptable, it may be necessary to call back workpieces that have already been dispatched or that are even already in use, which causes important loss of money, along with other disadvantages. Moreover, the above-mentioned procedures do not allow real-time adjustments of the process variable, in order to limit hydrogen absorption into the workpieces during the treatment, nor do they improve process efficiency.

The same also applies for treatments in which the surface of a metal workpiece is treated with an acid solution in order to remove an oxide surface layer. For example, pickling normally occurs by hydrogen production, which may cause hydrogen embrittlement. Moreover, the acid solution may be aggressive for the metal.

Therefore, a device is needed by which hydrogen absorption can be continuously followed in a galvanic treatment, or in treatments like pickling, such that real time data are available and, preferably, by which a process control can be carried out in order to prevent hydrogen embrittlement.

It is also known that the enamelling processes of metal workpieces may result into hydrogen absorption and surface embrittlement of the treated workpieces. In fact, when preparing the enamel frit, temperatures are normally achieved between 800° C. and 850° C. In these conditions, some water present in the enamel mixture is catalytically dissociated by the iron of the steel of the metal workpiece, therefore hydrogen is formed that is absorbed into the workpiece and then diffuses through the workpiece. In the subsequent cooling of the workpiece, hydrogen tends to migrate back to the surface of the workpiece, where it encounters an impervious enamel layer. The pressure of hydrogen may deteriorate and weaken this layer. This is the so called "fish scale" defect.

Therefore, a device is needed for preliminary permeation tests, in order to assess whether a metal workpiece can be enamelled without causing such behaviour.

The device traditionally used for preliminary permeation tests is the Devanathan-Stachurski cell, which comprises a hydrogen generation half-cell and a measurement half-cell. The cell allows measuring hydrogen diffusivity in a metal. This device is complicated since there are two half-cells that must be mounted together, since a tight connection must be ensured and for further minor reasons. Moreover, the tests have a considerable duration. Therefore, a device is needed for carrying out hydrogen permeation preliminary tests or for measuring hydrogen diffusivity through a metal material, which is more user-friendly and more reliable than the prior art devices.

In order to measure the content of hydrogen within metal workpieces, devices known as desorbers are used, which comprise an oven in which a sample, is arranged after enclosed within a quartz tube. The sample is then heated in order to cause absorbed hydrogen to come out of it, and to leave the oven in a gas stream. The hydrogen concentration in the stream is monitored, integrated and compared with the weight of the sample, thus obtaining a quantitative measure of the hydrogen contained in the sample. The desorbers are rather cumbersome and expensive, and also involve considerable operation and maintenance costs. Moreover, they only allow destructive tests. Therefore, a device is needed for determining the content of hydrogen incorporated in a metal workpiece that is less expensive, that involves lower operation and maintenance costs, and that is more user-friendly than conventional desorbers. Such a device is also needed for performing nondestructive tests.

It is also known that at least one step of the corrosion processes in a metal material occurs by producing hydrogen. This hydrogen production depends upon the corrosion intensity. Devices are also known for monitoring the flow of hydrogen as an indicator of corrosion events. These devices comprise amperometric sensors, so they do not provide a satisfactory reliability and strength.

As is well known, hydrogen is more and more used as an energy vector/fuel, for example, for powering motor vehicles. In particular, hydrogen gas distribution facilities and networks are developed comprising self-service pumps. For safety of such installations, devices are required for real time checking whether hydrogen embrittlement can occur in the metal of the ducts and of the gas bottles used for conveying and storing hydrogen gas. Nowadays, no device is known that can reliably detect and notify this hydrogen embrittlement risks.

US2009/0277249A1 describes a method and a device for determining the quality of a seal element by bringing a hydrogen-containing mixture into contact with the seal element and by measuring the amount of hydrogen that passes through the seal element, in the form of molecular hydrogen. The use is also mentioned of the same technique for carrying out permeation tests in a component, wherein hydrogen passes through the component, still in the molecular form. The technique does not allow determining the content of hydrogen that is present in the seal element, and does not allow determining hydrogen diffusivity through the seal element. Therefore, US2009/0277249A1 cannot assess the risk of embrittlement of the seal element, but the tightness degree of the seal element, i.e. how much hydrogen is lost through the seal element.

In EP1114992A2 a cap-shaped collection element is used that is provided with spiral-shaped ribs for collecting hydrogen coming from a surface of a workpiece, and an amperometric sensor is also used.

WO2011/131897A1 describes a process for monitoring the corrosion rate in a metal duct that conveys a corrosive fluid, in which a device is provided that is arranged to form, when the device is installed on a wall of the metal duct, a chamber configured for receiving hydrogen gas that permeates through the wall of the duct. The process comprises a treatment step for eliminating a metal species from the chamber, a step of measuring an amount of hydrogen that is received in the chamber, in order to estimate the corrosion rate of the duct metal. Even in this case, the measurement of permeated hydrogen is a permeability measurement, which increases due to the corrosion, but it cannot lead to the content of hydrogen that is present in the walls of the duct, nor can hydrogen diffusivity in the walls be determined.

SUMMARY OF THE INVENTION

It is therefore an object of the present invention to provide a device for detecting the presence of hydrogen within a metal workpiece or article, and for assessing whether a corrosion process, or a hydrogen embrittlement risk is likely to occur.

It is a particular object of the present invention to provide such a device for establishing whether hydrogen is present in metal workpieces, and for assessing the risk of corrosion cracking due to hydrogen embrittlement for metal workpieces during a treatment that involves hydrogen production, such as a galvanic treatment, pickling, chemical milling or electropolishing.

It is another particular object of the present invention to provide such a device for carrying out hydrogen permeation preliminary tests on a metal, in order to evaluate hydrogen diffusivity, and/or in order to foresee the behaviour of a workpiece of the same metal in a surface treatment like an enamelling process.

It is a further particular object of the present invention to provide such a device for establishing whether hydrogen is present in workpieces of equipment, and for assessing the hydrogen-related risks for workpieces of equipment such as piping and vessels for conveying and/or treating and/or storing hydrogen gas, to be used, for instance, in distribution facilities for motor vehicles.

It is also a particular object of the present invention to provide such a device for identifying a corrosion process by hydrogen permeation measurements in piping and vessel elements used in the chemical/energy production industry.

It is a particular object of the invention to determine the content of hydrogen that is present in a workpiece and/or hydrogen diffusivity through the workpiece, as well as to correlate such content and/or diffusivity with the risks of cracking of the workpiece due to hydrogen weakening or embrittlement rate. These and other objects are achieved by a device for measuring a content of hydrogen absorbed by permeation in a workpiece in the form of hydrogen atoms, in order to characterize an interaction between the workpiece and the absorbed hydrogen which can weaken or cause an embrittlement of the workpiece, the device comprising:

a probe comprising:
  a collection means configured for receiving an amount of absorbed hydrogen emanating from the workpiece;
  an inlet port for a measurement gas, in particular for environmental air;
  a mixing chamber arranged to pneumatically communicate with the inlet port, and with the collection element configured for mixing the measurement gas with the amount of hydrogen emanating from the workpiece, such that a gaseous mixture is formed in which the amount of hydrogen emanating from the workpiece is changed from the atomic form into a molecular form;
a solid-state sensor arranged to measure a hydrogen concentration in the gaseous mixture, the solid-state sensor pneumatically connected with the mixing chamber, so as to come into contact with the gaseous mixture, the solid-state sensor configured to generate a measurement signal responsive to the hydrogen concentration of the gaseous mixture;
a gas transfer means arranged for creating a flux of the measurement gas from the inlet port towards the solid-state sensor, at a predetermined flowrate, the flow arranged to assist the gaseous mixture to form in the mixing chamber and to come into contact with the solid-state sensor; and
a processor means functionally connected to the solid-state sensor, so as to receive the measurement signal, the processor means comprising a program means configured for processing the measurement signal and for calculating at least one parameter related to the interaction between the workpiece and the absorbed hydrogen.

Solid-state sensors, per se known, are used also for hydrogen, but only to measure the hydrogen concentration in gas-hydrogen mixtures which may form in the environment, and not for measuring the hydrogen absorbed in workpieces of metal or of other material, and emanating through a surface of these workpieces. The advantage of using solid-state sensors is that they do not comprise electrodes, therefore they do not require using specific liquids or gels i.e. chemical substances that may be toxic or harmful.

The process of permeation of hydrogen, which absorbed in the form of hydrogen atoms, through the workpiece occurs due to an of absorbed hydrogen concentration gradient between the inside of the workpiece and the environment surrounding it, where hydrogen is present in the form of molecules, and has a very low concentration, normally about 0.5 ppm.

In a device according to another exemplary embodiment, the collection element of the probe comprises an access opening for the amount of emanating hydrogen, and comprises a means for arranging the probe with the access opening facing the workpiece, such that the amount of hydrogen emanating from the workpiece passes through the access opening. So as to enter into the mixing chamber. Such a device is useful for performing measurements starting from the hydrogen absorbed in the workpiece.

In particular, the means for arranging the probe with the access opening facing the workpiece is configured for fastening the probe with the opening arranged in contact with the workpiece. The fixing means may be a conventional fixing means, in particular it may comprise a mechanical means such as a screw-threaded means, a flange means as well as a welded means. In alternative, or in addition, the fixing means may be a magnetic means, for instance it may comprise at least one portion of the probe made of a magnetic material, if the workpiece comprises a metal that can be attracted by a magnetic material.

The objects of the invention are also reached by a method for measuring an amount of hydrogen emanating from a workpiece, in order to characterize an interaction between the workpiece and the hydrogen absorbed in the workpiece in the form of hydrogen atoms, the method comprising the steps of:
  arranging a mixing chamber proximate to the workpiece, such that the mixing chamber is accessible to the amount of hydrogen emanating from the workpiece;
  introducing a stream of a measurement gas, in particular of environmental air, into the mixing chamber at a predetermined flowrate;
  forming a mixture of the measurement gas and of the amount of hydrogen emanating from the workpiece in the mixing chamber;
  conveying the mixture to a solid-state sensor;
  measuring through the solid-state sensor a hydrogen concentration in the gaseous mixture, the step of detecting comprising a step of generating a measurement signal responsive to the hydrogen concentration; and
  processing the measurement signal, and calculating at least one parameter related to the interaction between the workpiece and the hydrogen absorbed in the workpiece in the form of hydrogen atoms.

In an application of the method, a device that has a probe with an opening for introducing the workpiece therein can be used for detecting and/or monitoring a risk associated with the presence of hydrogen absorbed in the workpiece in the form of hydrogen atoms, such as the risk of hydrogen embrittlement in metal workpieces that are used in contact with a hydrogen-containing gas. In this case, the step of arranging a mixing chamber provides a step of arranging an access opening the mixing chamber facing an outer surface of the wall, in particular the access opening is brought into contact with the wall. Moreover, a step is provided of sucking gas from the mixing chamber, thereby causing the steps of introducing a stream of a measurement gas, of forming a mixture and of conveying the mixture. Moreover, the step of processing the measurement signal calculates a value C of content of hydrogen absorbed in the wall as the interaction parameter. In particular, the control step calculates a plurality of distribution values of the hydrogen absorbed in the workpiece. To calculate the plurality of distribution values a finite element method can be used starting from the measurement signal, which changes over time.

In particular, the device can be used for monitoring the risk of hydrogen embrittlement in walls of containers such as piping elements, vessels and other equipment that is used for conveying, storing and transforming a hydrogen-containing gas in a distribution or manufacturing process.

In another application of the method, such a device can be used for detecting and/or monitoring over time the corrosion of the wall of a container used for conveying, storing or to transforming a corrosive liquid. In this case, the method differs from the case of detecting and/or monitoring a risk of embrittlement in that, the step of processing the measurement signal calculates a value of corrosion rate of the wall due to the corrosive fluid as the interaction parameter.

The container may be a piping element, a storage vessel or a process equipment. As well known, in a wide range of metal materials, corrosion occurs along with a reduction reaction of hydrogen, and with a production of hydrogen gas, as soon as the conditions for a reduction of oxygen in the environment surrounding the corrosion site are no longer present. The metal of the wall proximate to the corrosion site is permeated by a portion of the hydrogen produced this way. Therefore, the concentration of hydrogen in the gaseous mixture that is formed within the probe provides a measure of the corrosion process, even of a generalized corrosion process, within such a container. In other words, the flow of hydrogen emanating from a workpiece affected by corrosion can be correlated to corrosion rate and so to weight/thickness loss of the wall, which allows predicting the possibility of breaking, for instance, due internal pressure or other loads.

In an exemplary embodiment, the probe comprises a spacer duct that has a first end provided with said opening, and a second end, opposite to the first end, that is pneumatically connected with the mixing chamber. Advantageously, in the case of containers that operate at high temperatures, typically beyond 150° C., the length of the spacer duct is selected so that the temperature at the sensor does not exceed a predetermined maximum temperature, in order to ensure the operation of the sensor and/or not to reduce its useful life.

This way, it is possible to detect and/or to monitor corrosion processes, and/or hydrogen embrittlement risks, respectively in the case of containers used for treating corrosive fluids, and/or for treating gas that may contain hydrogen, even at high temperature. In particular, the device according to this exemplary embodiment of the invention can be used for detecting and monitoring hydrogen-related damage events, such as Hydrogen embrittlement and Hydrogen disbonding, i.e. the detachment of an inner lining layer due to hydrogen in a cooling step. This is particularly useful in the case of the hydrocracking reactors.

In another exemplary embodiment, the device comprises a means for displacing the probe while maintaining the opening at a predetermined distance from a surface, along a prefixed movement path. In particular, the means for displacing the probe is an automatic means for displacing the probe according to a prefixed time program, or following the movement of a distinct apparatus. In a further application of the method, such a device can be used for measuring the hydrogen gas that is generated while welding two metal elements by an automatic procedure, in which a weld bead is formed. To this purpose, the device may comprise a conventional connection means to be connected with a welding head of an automatic welding equipment. Since the opening is at a distance from the metal elements to be welded, also measurement air is sucked from the environment through the opening. Moreover, the method has a difference with respect to the case of detecting and/or monitoring the risk of embrittlement in a metal workpiece used in contact with a hydrogen-comprising gas, since the step of arranging a mixing chamber comprises a step of moving the mixing chamber following a front of the weld bead being formed, at a predetermined distance from the metal workpieces.

This way, it is possible to detect and monitor, over time, the content of residual hydrogen absorbed in the weld bead, which is the main cause of the collapse event known as cold cracking.

In an exemplary embodiment, the device also comprises an apparatus for performing electrochemical permeation tests in said workpiece, the apparatus comprising:
- a hydrogen gas source configured for generating a measurement hydrogen gas on a first face of the sample opposite to a second face of said workpiece, where said element of collected is arranged;

wherein the program means is configured to calculate an interaction parameter selected from the group consisting of:
- a diffusion coefficient or diffusivity of the material;
- an average content of hydrogen absorbed in the workpiece; and
- a distribution of hydrogen absorbed in the workpiece.

In particular the hydrogen gas source is an hydrogen-generating electrolytic cell comprising an anode and a cathode arranged to be brought to a working voltage, and an electrolytic solution arranged between the anode and the cathode, wherein the cathode has a voltage equal to the voltage of the sample, which is made of a metal material, and the sample has the first face in contact with the electrolytic solution, wherein the voltage and the electrolytic solution are selected so as to cause a reduction reaction of the measurement hydrogen on the first face.

This way, a device is provided for performing permeation measurements advantageously with respect to the prior art devices, for instance with respect to the above-mentioned Devanathan-Stachurski cell. In fact, the device comprises only one electrolytic hydrogen generation half-cell, on the contrary it does not comprise a measurement electrolytic half-cell.

Therefore, a further electrochemical solution has not to be used for the measurement, whereby:
- some corrosion events are prevented, since the sample does not have anodic face exposed to this measurement solution;
- the sample must not be passivated before the permeation test, which saves time; and
- an accurate preliminary treatment of the surface of the sample, i.e. a mechanical treatment and a cleaning treatment, is not required, as it is, on the contrary, in an electrochemical measurement.

Besides determining the diffusivity, the device can also be used for carrying out preliminary tests for preliminarily evaluating the strength of an enamel layer on a metal surface, by treating a sample, before enamelling the finite workpieces.

In an exemplary embodiment, the probe of the device comprises a container configured to house the workpiece, such that the amount of hydrogen emanating from the workpiece forms the gaseous mixture with the measurement gas in this container, and the processor means is configured for:
- calculating a flow value over time of the hydrogen emanating from the workpiece starting from the flowrate of the measurement gas and from the absorbed hydrogen concentration; and
- calculating, as the parameter related to the interaction, a hydrogen absorption parameter, in particular an average content of hydrogen absorbed in the workpiece, by integrating in the time the amount of hydrogen emanating from the workpiece time, over a predetermined time interval.

This way, the invention allows measuring the release of hydrogen from bodies, for example metal bodies such as mechanical workpieces like bolt elements, providing a cheaper and more user-friendly alternative to the currently known desorbers. A particular advantage is the possibility to avoid using an industrial gas such as nitrogen and argon for carrying out the measure. This involves into lower costs, a greater user-friendliness and better safety conditions. Besides, the measurement can be carried out in a shorter time, since no calibration is required to take into account the presence of the above-mentioned industrial gases.

In an exemplary embodiment, the device may comprise a means for heating the workpiece, for instance an electric or induction heating means, in order to assist hydrogen to emanate out of the workpiece.

In particular, the processor means is configured for calculating a plurality of distribution values of the content of the hydrogen absorbed in the workpiece. Preferably, the processor means is configured for using a finite element method in order to calculate the plurality of distribution values starting from the measurement signal, responsive to the time.

With such a device it is also possible to know the hydrogen content remaining at a given temperature, for example, at a working temperature of the workpiece.

A device according to a further particular exemplary embodiment of the invention is suitable for measuring a content of hydrogen absorbed in a metal workpiece that is receiving a treatment in a chemical or electrochemical bath, this treatment taking place by a hydrogen gas production on a surface of said metal workpiece, and in this device:
- the probe has a metal shell that defines the mixing chamber;
- the probe is configured for being at least partially immersed into the treatment bath;
- the metal shell itself is configured for receiving the treatment on an own outer surface exposed to the treatment bath and to be permeated by a further quantity of permeation hydrogen, such that the permeation hydrogen permeates through the metal shell and has enters into the mixing chamber; and
- the processor means is configured for calculating, as the parameter related to the interaction between hydrogen absorbed and the metal workpiece, a parameter selected from the group consisting of:
  - a content of hydrogen absorbed in said metal workpiece;
  - an efficiency parameter of said treatment, more in particular, a cathode efficiency parameter of said treatment.

In particular, the processor means is configured for calculating a plurality of distribution values of the content of hydrogen absorbed in the metal workpiece. Preferably, the processor means is configured for using a finite element method for calculating the plurality of distribution values starting from the measurement signal, responsive to the time.

In an advantageous exemplary embodiment, the probe comprises a tubular body that has a first end pneumatically connected with the inlet port for the measurement gas and has a second end connected to an outlet port for the mixture of the measurement gas and of the absorbed hydrogen, through which the sensor is pneumatically connected with the mixing chamber. For example, the tubular body can be a U-bent metal tube, configured for being immersed with its own central portion into the treatment bath, the end portions of the tube remaining out of the treatment bath.

The device according to this particular exemplary embodiment is configured to indirectly measure the content of absorbed hydrogen that is formed on a metal workpiece while receiving a surface treatment in an electrochemical bath, in which the metal workpiece is at a cathodic voltage or at an anodic voltage. For instance, this treatment may be an electrochemical coating metal deposition process such as silver coating, galvanization, cadmium coating, chrome plating, or an electropolishing treatment.

The device according to this exemplary embodiment is also suitable for measuring hydrogen absorbed during a treatment of a metal workpiece that takes place in a chemical bath, i.e. in a solution that can interact with the metal workpiece causing, for example, an surface oxidation, such as a pickling treatment, or a chemical milling treatment.

Moreover, the device according to this particular exemplary embodiment allows evaluating the quality of the treated workpieces in a very short time and non-destructively, in particular in a galvanic treatment. Substantially real-time learning hydrogen absorption conditions, or in any case learning them in a time much shorter than what is allowed by the conventional methods, makes it possible to reject and possibly to treat workpieces containing too much absorbed hydrogen before shipping them, thus reducing the number of late recalls or even avoiding failure after installation. Besides, the device according to this particular exemplary embodiment is useful for controlling the above-mentioned treatment processes. In other words, the device allows real-time adjusting the operating parameters of the treatment bath, so as to correct possible excessive hydrogen absorption. Real-time learning the true content of absorbed hydrogen also allows such to assess whether degassing the workpieces can be avoided after the treatment, in order to reduce production costs and times.

BRIEF DESCRIPTION OF THE DRAWINGS

The invention will be now shown with the description of its exemplary embodiments, exemplifying but not limitative, with reference to the attached drawings in which.

DESCRIPTION OF A PREFERRED EXEMPLARY EMBODIMENT

Figure 1:
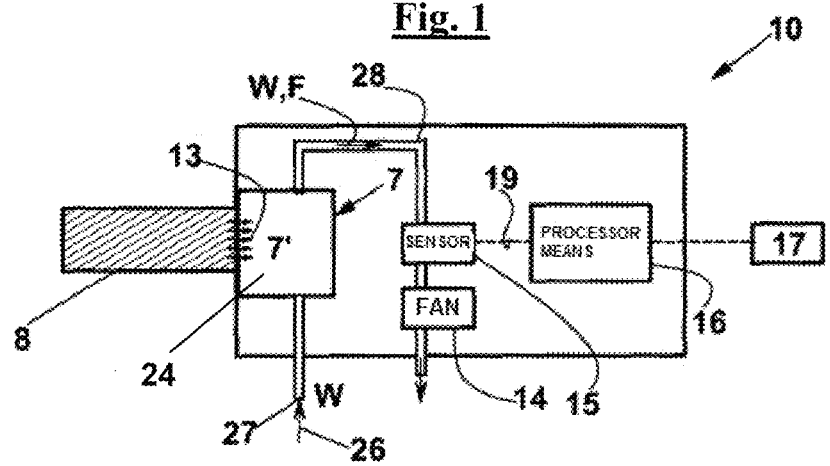
FIG. 1 diagrammatically shows a device according to the invention.

With reference to FIG. 1, a device 10 is described for measuring a hydrogen 13 emanating from a workpiece 8, in order to characterize an interaction between workpiece 8 and a content of hydrogen absorbed in workpiece 8. The device comprises a probe 7 that includes a mixing chamber T that is accessible to hydrogen 13 that emanates from workpiece 8 due to the presence of hydrogen absorbed therewithin, and that is equipped with an inlet port 27 for a measurement gas 26. The inlet port can be an environmental air intake port or a nozzle suitable for connection to a container like a gas bottle, containing a pressurized gas, e.g. air, not shown. Device 10 also comprises a solid-state sensor 15, and a connection means 28 for pneumatically connecting sensor 15 with mixing chamber 7'. Device 10 further comprises a gas conveying means 14 for conveying the measurement gas from inlet port 27 towards solid-state sensor 15, at a predetermined flowrate W. Due to the conveying means, a mixture 24 is formed in mixing chamber 7 by hydrogen 13 emanating from workpiece 8 and by measurement gas 26, which is conveyed to solid-state sensor 15 through connection means 28. Sensor 15 is configured for measuring a hydrogen concentration F in gas mixture 24, and for generating a measurement signal 19 that depends upon concentration F.

Figure 10:
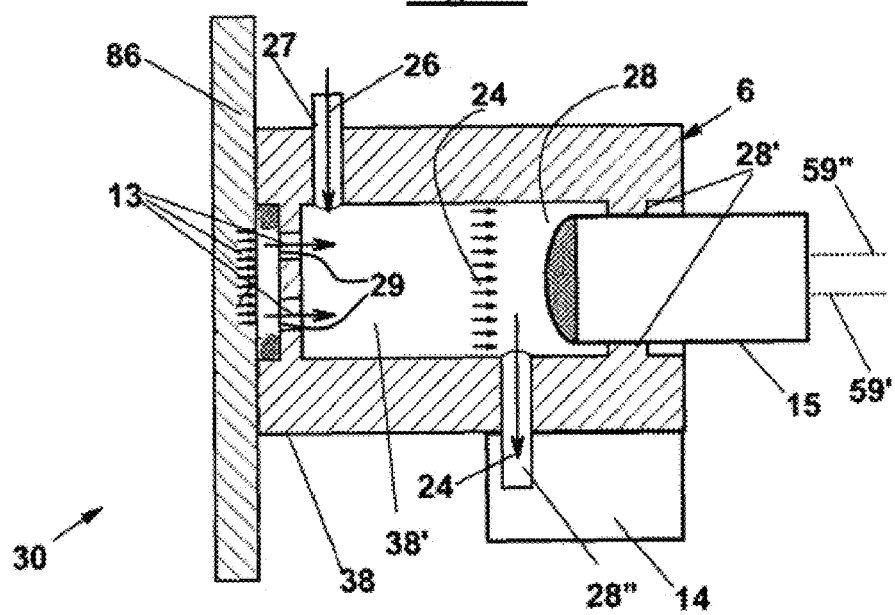
FIG. 10 shows an integrated device according to the invention.

In the exemplary embodiment of FIG. 1, the gas conveying means may comprise a fan 14, which is preferably arranged downstream of sensor 15, or downstream of a chamber accessible to sensor 15. In another exemplary embodiment, fan 14 may be located between mixing chamber 7 and sensor 15. In particular, as shown in FIG. 10, the probe and the sensor may form a compact device in which sensor 5 is arranged in an inner portion of probe 7.

In an exemplary embodiment, not shown, the conveying means can comprise a flow adjustment means, for example a regulation valve, associated with a pressurized gas container like a gas bottle.

Device 10 also comprises a processor means 16 functionally connected to solid-state sensor 15, so as to receive measurement signal 19. Processor means 16 is adapted to process measurement signal 19 for calculating a parameter 17 characterizing the interaction between workpiece 8 and the hydrogen absorbed therewith in.

Figure 2:
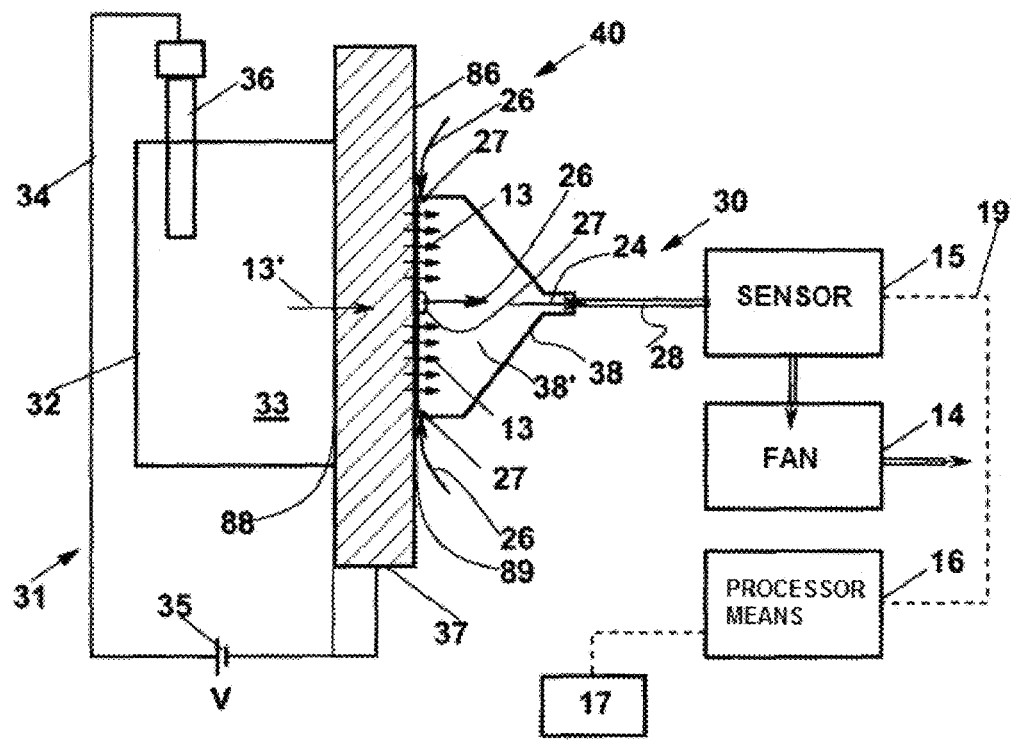
FIG. 2 diagrammatically shows an apparatus for carrying out electrochemical hydrogen permeation tests in a sample, comprising a device according to the invention.

With reference to FIG. 2, a permeation test apparatus 40 is described for performing electrochemical permeation tests in a sample 86. Device 40 comprises a hydrogen gas generation means 31 for generating measurement hydrogen gas 13'. In an exemplary embodiment shown, the generation means comprise an electrolytic gas generation unit, i.e. a generation cell 31. Generation cell 31 comprises a container 32 which, in use, contains a generation solution 33, and a circuit 34 comprising a voltage generator 35 and an anode 36 that is arranged within container 32 and that is immersed in generation solution 33. Anode 36 is connected to the positive pole of generator 35. The negative pole of generator 35 may be connected to a cathode 37. If sample 86 is made of a metal material, cathode 37 may comprise or may be in contact with sample 86. Generation solution 33 may be selected by taking into account the application for which the preliminary permeation test is carried out. In the case of an enamelling treatment, the generation solution may be a NaOH solution of an H2SO4 solution also containing hydrogen production promoters. In the case of a pickling treatment, generation solution 33 may be a conventional pickling bath.

In apparatus 40, sample 86 is electrically arranged at the same voltage as cathode 37 of generation cell 31, therefore a hydrogen reduction reaction can take place on sample 86, and hydrogen permeates through the material in the form of hydrogen atoms and then comes out of it as gaseous molecular hydrogen 13.

Figure 3:
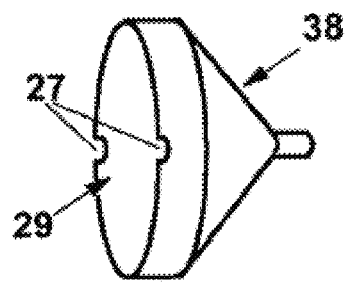
FIG. 3 is a perspective diagrammatical view of the probe of the device of FIG. 2.

Apparatus 40 further comprises a device 30, according to the invention, for measuring the content of hydrogen that is absorbed in sample 86. Device 30, according to the invention, comprises a probe 38. The probe can be a substantially bell-shaped element 38, as shown in FIG. 3, that includes a mixing chamber 38', equipped with an access opening 29 for hydrogen amount 13 emanating from sample 86, and also equipped with at least one inlet port 27 for introducing environmental air 26, as the measurement gas. The probe is also equipped with a means, not shown, for arranging probe 38 so that opening 29 faces workpiece or sample 86, in this case a fixing means is preferably provided on sample 86.

Device 30 further comprises a solid-state sensor 15, as well as a gas transfer means, e.g. a fan 14. A pneumatic connection means 28 is also provided between mixing chamber 38' and fan 14. In particular, the pneumatic connection means may comprise a sensor housing 15 within probe 38, with which sensor 15 forms a compact device, as shown in FIG. 10.

Hydrogen the amount 13 emanating from sample 86 enters into mixing chamber 38' of probe 38 through opening 29. In mixing chamber 38', amount of emanating hydrogen 3 is mixed with the air sucked through port 27 due to fan 14, forming an air/hydrogen mixture 24. Mixture 24 reaches sensor 5, due to the suction of fan 14. Sensor 15 is configured to produce an electric signal 19 responsive, in particular proportional to the hydrogen concentration of mixture 24 analysed on-line. The electronics of sensor 15 is electrically connected to processor unit 16 in order to provide it with signal 19. In processor unit 16, signal 19 can be processed to determine diffusivity D of hydrogen in sample 86, and an average concentration value of the hydrogen permeated into sample 86.

Figure 12:
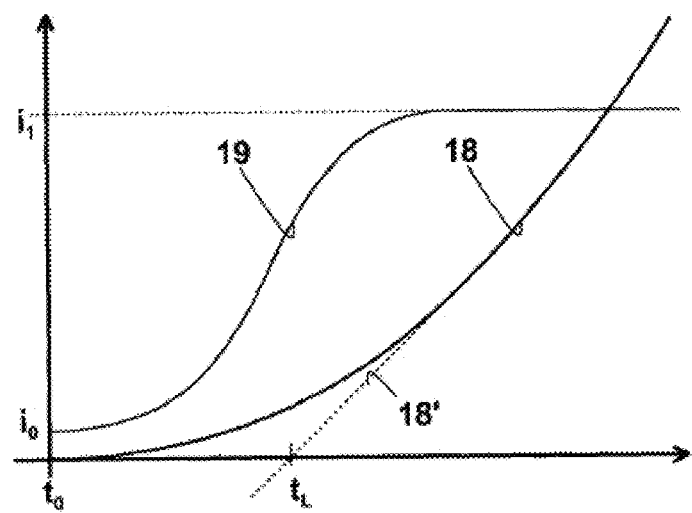
FIG. 12 diagrammatically shows a process for determining the diffusivity.

Diffusivity D may be determined by the same well-known procedure used in the prior art, by the Devanathan-Stachurski cell. More in detail, with reference to FIG. 12, measurement signal 19, for example an electric current signal i(t) is shown as a current-time plot that starts at a test initial time to, grows from a value $i_0$, and then maintains a substantially constant value $i_1$. The signal is integrated over time between initial time $t_0$ and a generic time t, obtaining a function 18 that approximates a straight line 18' as better as signal 19 is close to value $i_1$. The intersection point of line 18' with time axis indicates a time $t_L$, known as time-lag, which allows calculating diffusivity D by the formula $D=\sigma^2/6t_L$ in which σ is the thickness of the sample.

In an enamelling preliminary test, besides the step of calculating diffusivity D, a step is provided of measuring the permanence time of the hydrogen when passing through sample 86, and a step is also provided of calculating free hydrogen content $C_L$ within sample 86.

By such determinations, the enamelling process can be made compliant with EN10209, UNI9904, UNI8763 rules.

The average content of the permeation hydrogen within sample 86 may be determined by integrating signal 19 (FIG. 12) over a predetermined time range $t_0$-$t_1$ starting from test initial time $t_0$.

With reference to FIG. 10, an exemplary embodiment is described of an integrated device 30, in which an elongated body 6 includes mixing chamber 38' of probe 38', and a housing 28 for sensor 15, which provides a pneumatic connection of sensor 15 with mixing chamber 38. Elongated body 6 has a fixing means, not shown, for fixing of one of its own ends to workpiece 86. At the same end, elongated body 6 has two access openings 29 for introducing hydrogen 13 emanating from workpiece 86, into mixing chamber 38'. At the opposite end of elongated body 6, where housing 28 for sensor 5 is provided support elements 28' for sensor 15 are also present. The space between inlet port 27 and housing 28 defines a mixing chamber 38', for creating mixture 24 of the hydrogen 13 and of measurement air 26. At housing 28, body 6 also has an outlet port 28" for gaseous mixture 24. Outlet port 28" is pneumatically connected with a fan 14 integral to elongated body 6.

Solid-state sensor 15 may be, for instance, a MikroKera 4 L Hydrogen Sensor available from Sinkera Technologies Inc.

Figure 4:
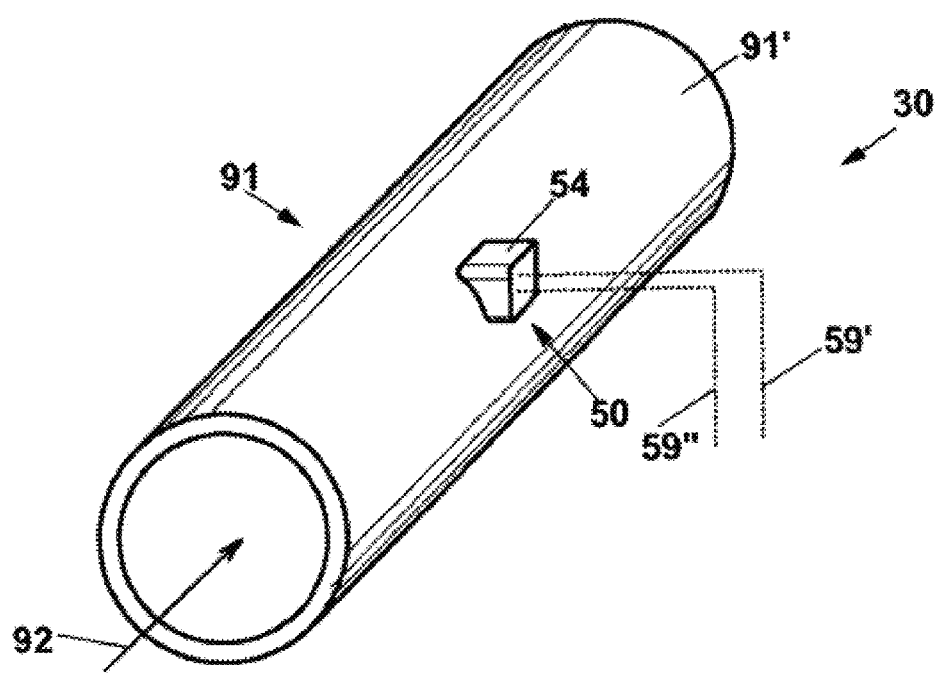
FIGS. 4 and 5 diagrammatically show a device for monitoring the hydrogen absorbed in the wall of a container of hydrogen gas, or for following the corrosion of a wall of a container of a corrosive fluid.
Figure 5:
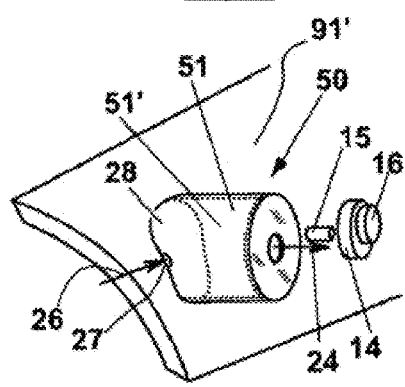
Figure 6:
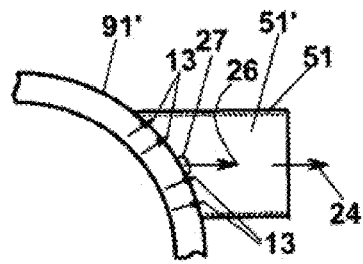
FIG. 6 is a diagrammatical cross sectional view of the probe of the device of FIGS. 4 and 5.

With reference to FIGS. 4-6 a device 50 is described, according to an exemplary embodiment of the invention, for monitoring the condition of shell portions arranged to contain corrosive fluids at room temperature, for example, in the petrochemical industry. FIG. 4 shows a container 91, such as a piping element, that contains, or more in particular conveys a corrosive process liquid 92. Device 50 is mounted to the outer face of the metal wall 91 of container 91 by a conventional means, for example by a magnetic means if this is allowed by the material of container 91. Advantageously, device 50 has an electric supply connection 59' and, preferably, a data connection means 59" for outputting data computed by processor unit 16, according to the diagrammatical view of FIG. 1. More in detail, as shown in FIG. 5, device 50 comprises a probe 51 that includes a mixing chamber 51'. Probe 51 is also equipped with an inlet port 27 for environmental air at the portion adjacent to the wall 91 or proximate to it, and also with a housing 28 for a solid-state probe 51, in order to pneumatically connect probe 51 and mixing chamber 51', in a portion of probe 51 at a distance from wall 91.

Probe 51 comprises a means for fixing to the outer surface of wall 91', not shown, for example a magnetic fixing means. Hydrogen 13 emanating from sample 86 enters into mixing chamber 51' through opening 29. In mixing chamber 51', hydrogen 13 is mixed with air sucked through inlet port 27 by fan 14, thus forming an air/hydrogen mixture 24. Mixture 24 reaches sensor 15, due to the suction of fan 14. Sensor 15 is configured to produce an electric signal 19 responsive, in particular proportional to the hydrogen concentration of mixture 24 analysed on-line. The electronics of sensor 15 is electrically connected to processor unit 16 in order to provide it with signal 19. In processor unit 16, signal 19 is processed to obtain a value of concentration of hydrogen permeated into wall 91'. Probe 51, sensor 15, fan 14 and processor means 16 may be enclosed in a box 54 arranged to be connected to wall 91' of container 91. More in particular, device 50 can be a compact device, as shown in FIG. 10.

The method provides a step of calculating the true local hydrogen concentration C in the metal, starting from measurement signal 19 of the flow φ of hydrogen, by a finite element method, as indicated above. In alternative, or in addition, a step is provided of determining a rate of the corrosion in the metal due to the corrosive fluid.

Device 50 of FIGS. 4, 5 and 6 can also be used for performing hydrogen permeation measurements, in order to assess the risks associated with hydrogen absorbed by permeation, such as the risks of hydrogen embrittlement of a metal wall 91' of a container 91 used for containing a hydrogen-comprising gas 92 or a fluid 92 that can give rise to hydrogen. More in detail, device 50 can be used for assessing the presence of a hydrogen content C higher than a predetermined embrittlement content value C*, above which a significant risk arises of hydrogen embrittlement of wall 91', for example. In this case, processor means 6 is configured for calculating a value C of the content of hydrogen within wall 91' starting from measurement signal 19 related to the hydrogen concentration in gas mixture 24.

Figure 7:
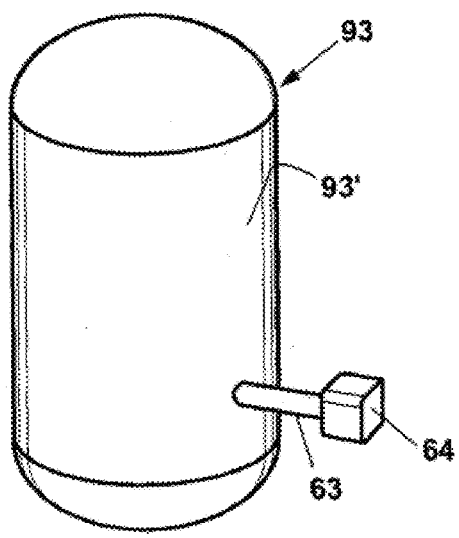
FIGS. 7 and 8 diagrammatically show a device similar to the device of FIGS. 4 and 5, suitable for working at high temperature.
Figure 8:
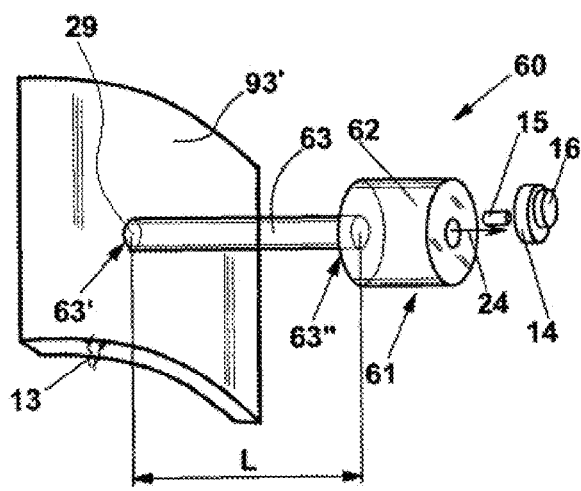

With reference to FIGS. 7 and 8, a device 60 is described, according to an exemplary embodiment of the invention, for monitoring the condition of containers arranged to contain corrosive fluids at a high temperature, at which a solid-state sensor cannot operate. FIG. 7 shows a container 93, such as a vessel, that contains a corrosive process liquid. Device 60 comprises a probe 61, in turn comprising a mixing chamber 62 in which the solid-state sensor 15 is arranged, and also comprising a spacer 63, in this case a tubular spacer, for maintaining sensor 15 and processor means 16 at a distance from wall 93' of vessel 93. Spacer 63 has a first end 63' facing the outer surface of wall 93' and a second end, opposite to the first end, pneumatically connected with mixing chamber 62. Tubular spacer 63 has a length L adapted to ensure that the temperature at mixing chamber 62 enables the solid-state sensor to work. Mixing chamber 62, sensor 15, fan 14 and processor means 16 may be enclosed in a box 64. More in particular, device 60 can be a compact device, as shown in FIG. 10.

In the exemplary embodiment of FIG. 8, the measurement portion 60 may comprise the same structure as device 50 of FIGS. 4-6. In other words, device 60 may differ from device 50 only in tubular spacer 63.

The step of processing is similar to what was described with reference to device 50. The step of processing may also comprise the steps of:
calculating the critical concentration above which a detachment from the wall of the reactor (disbonding) is possible;
calculating the critical concentration for HE; and
calculating the risk degree of hydrogen attack.

Device 60 of FIGS. 7 and 8 can also be used for performing hydrogen permeation measurements, in order to assess such risks as hydrogen embrittlement in a metal wall 93' of a container 93 used for containing a gas at high temperature, comprising hydrogen gas or a fluid that can give rise to hydrogen gas. More in detail, device 60 can be used for detecting the presence of a hydrogen content C higher than a determined embrittlement content value C*, above which a significant risks arises of hydrogen embrittlement of wall 93', for example. In this case, processor means 16 is configured for calculating a value C of the content of hydrogen in wall 93' starting from measurement signal 19 related to the hydrogen concentration in gas mixture 26.

Figure 9:
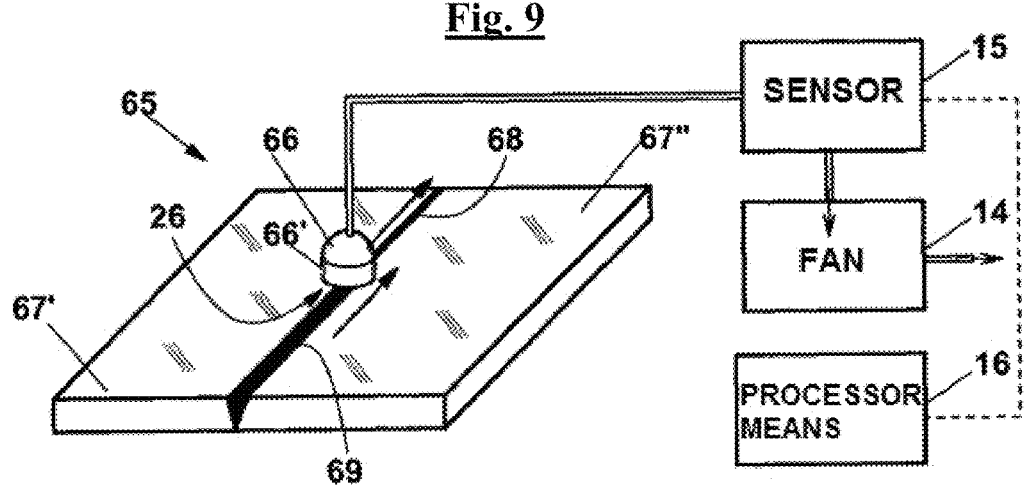
FIG. 9 diagrammatically shows a device for measuring hydrogen gas that is generated in an automatic welding process.

With reference to FIG. 9, a device 65 is described for measuring the hydrogen gas that is generated while welding two metal elements 67', 67" with each other, along a welding line 68, thus creating a weld bead 69, by an automatic procedure. Device 65 comprises a probe that may advantageously comprise a connection means to be connected with a welding head of an automatic welding equipment, not shown, or that can be associated with a means for displacing mixing chamber 66 synchronously with the welding head. Probe 66 is arranged at a distance from metal elements 67', 67", preferably at a distance of about a few mm, in order to suck environmental air 26 along with the hydrogen that is generated while welding, so that an air/hydrogen mixture 24 formed in a mixing chamber 66' of probe 66. Mixture 24 is conveyed towards a sensor 15 and is treated as in the previously described devices.

Processor means 16 of device 65 is also configured to carry out a step of calculating the risk degree of cold cracking due to hydrogen arising during a welding procedure.

Figure 11:
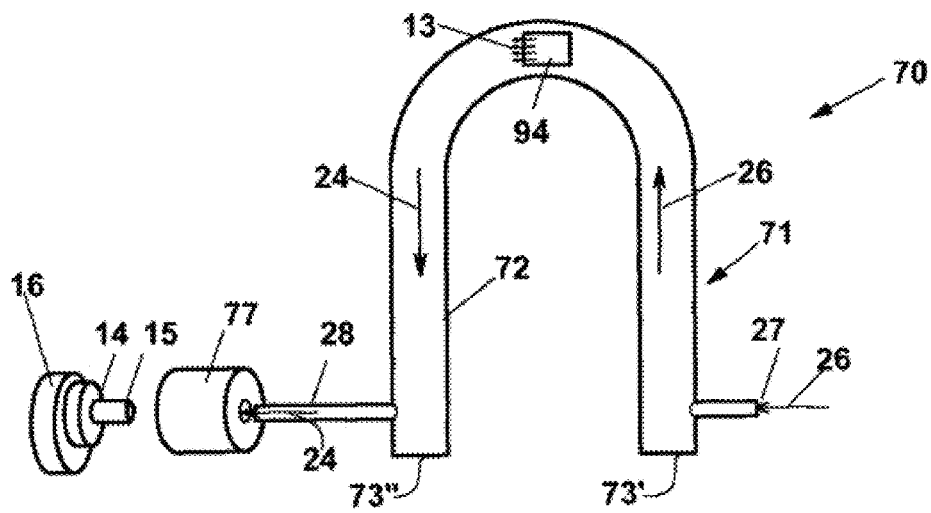
FIG. 11 diagrammatically shows a device for determining the content of hydrogen absorbed in a workpiece, in particular in a finished workpiece.

With reference to FIG. 11, device 70 is shown for determining the content of hydrogen retained in a workpiece, in particular in such a mechanical workpiece 94 as a bolt element. Device 70 comprises a probe 71 comprising a container 72, in this exemplary embodiment a "U"-shaped tube 72, arranged to receive workpiece 94. "U"-shaped tube 72 has two end portions 73' and 73" and has an inlet port 27 for introducing environmental air 26, proximate to end portion 73', and an outlet port 28 proximate to connection end portion 73", which form a pneumatic connection with a solid-state sensor 15. The solid-state sensor is mounted to a tubular support 77 along with a suction fan 14.

In an exemplary embodiment, device 70 may comprise a means for heating workpiece 94, e.g. a conventional electric or induction heating means, not shown.

Due to the surrounding flow of measurement air 26, and possibly to the heating step, sample 94 releases hydrogen 13 formed during a previous treatment as a gas. Hydrogen gas 13 and measurement air 26 sucked through inlet port 27 form a gaseous air-hydrogen mixture 24. Gas mixture 24 reaches sensor 15 through pneumatic connection means 28, due to the suction of fan 14. Sensor 15 is configured to produce an electric signal 19 responsive, in particular proportional, to the hydrogen concentration of mixture 24 analysed on-line, and therefore responsive to hydrogen amount 13 that workpiece 94, in the test conditions, releases subsequently. Signal 19 is processed as described with reference to the previous examples.

In this case, processor means 16 is configured to calculate a hydrogen flow value φ over time, starting from the flowrate W of measurement gas 26, which is known, for example, from the features of such a gas transfer means as a positive displacement fan, and starting from hydrogen concentration F of gas mixture 24, which is determined by sensor 15. Processor means 16 is also configured to calculate, in particular the average content $C_m$ of the hydrogen absorbed in workpiece 94, by integrating said flow of hydrogen contained in gas mixture 24, over a predetermined time interval.

Figure 13:
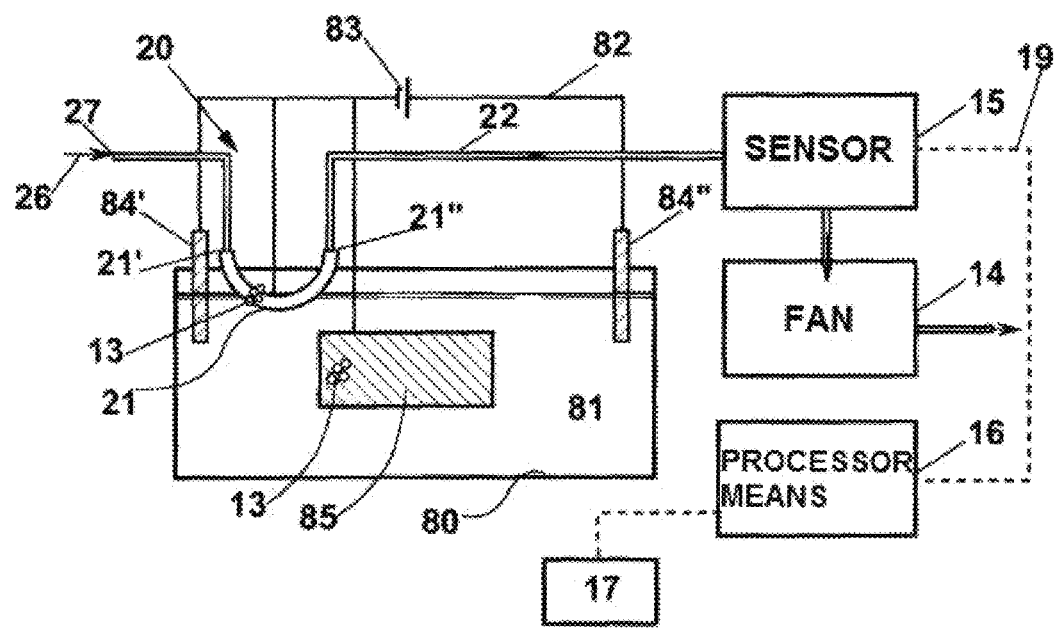
FIG. 13 diagrammatically shows a device for determining the content of hydrogen absorbed in a workpiece during a galvanic treatment.
Figure 14:
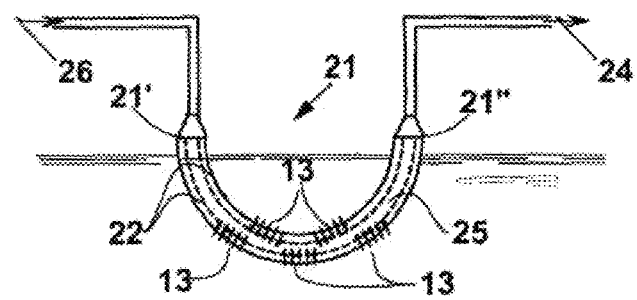
FIG. 14 shows in more detail, the probe of the device of FIG. 13, in a preferred exemplary embodiment.

With reference to FIG. 13 and FIG. 14, a device 20 is described for determining the content of hydrogen in a workpiece while being treated in an electrochemical bath, e.g. a galvanic treatment bath. A galvanic treatment device schematically comprises a treatment tank 80 arranged to contain a galvanic treatment solution or bath 81, an electric circuit 82, a voltage generator 83 arranged along electric circuit 82, a cathode element 84' and an anode element 84"

in use immersed within treatment solution 81 contained within tank 80. A workpiece 85 to be treated by a galvanic treatment is arranged within the tank 80, submerged with treatment solution 81.

Device 20 comprises a probe 21. Probe 21 may be made of any metal material, not necessarily the same as the material as workpiece 85 being treated, since the hydrogen reduction conditions depend upon the bath conditions. In use, an outer surface of probe 21 is partially submerged with solution 81 contained within tank 80, and the probe is electrically connected to cathode element 84'. In an exemplary embodiment, as shown, probe 21 comprises a U-shaped tube. Other shapes are possible, provided one end 21' of the tube can emerge from bath 81 to be connected to a measurement gas intake port, for example environmental air intake port. In alternative, probe 21 may comprise a coil-shaped element, not shown. One end 21" of "U"-shaped tube 21 is connected to solid-state sensor 5 through a duct 22.

During the galvanic treatment, some hydrogen gas 13 is formed both on the outer surface of probe 21 and on the outer surface of workpiece 85. In the case of probe 21, hydrogen 13 permeates into "U"-shaped tube 21 where it is mixed with measurement air 26 sucked by fan 14 through end port 21', thus forming an air/hydrogen mixture 24. Mixture 24 reaches sensor 15, due to the suction of fan 14. Sensor 15 is configured to produce an electric measurement signal 19 responsive, in particular proportional to the hydrogen concentration of mixture 24 analysed on-line. The electronics of sensor 15 is electrically connected to processor unit 16 in order to provide it with signal 19.

In processor unit 16, signal 19 is processed to obtain at least one parameter 17 that describes the interaction between absorbed hydrogen and probe 21, and, therefore, the interaction between absorbed hydrogen and workpiece 85. In particular, processor unit 16 is configured for calculating the values of a profile of the residual content C of hydrogen in workpiece 85, which can be compared with a maximum value of content C*, called the critical content, beyond which the risk of hydrogen embrittlement is unacceptable. Processor unit 16 may be configured for automatically carrying out this comparison, and to notify the result thereof to an operator through a conventional display means such as a digital or analog display means and/or an optical and/or acoustic alarm means.

In order to produce the values of a profile of content C over time, i.e. a plot of the residual hydrogen concentration in workpiece 85 versus time, processor means 16 may be configured for carrying out a finite element method.

In other words, by knowing diffusion coefficient D of hydrogen in the metal, critical content C*, as well as features of the workpiece such as the surface area S and the thickness T, it is possible to measure flow $\varphi$ of hydrogen 13 through the surface of probe 21. Therefore content C of hydrogen absorbed in the metal can be calculated as well. In particular, diffusion coefficient D can be calculated from flow $\varphi$. By comparing C with C*, it is possible to assess the hydrogen embrittlement risk of the workpiece.

Processor unit 16 may be further configured to calculate a cathode efficiency parameter $\eta_0$ of the process. Besides, processor unit 16 may be also configured to produce a control signal in a form that can be received by a control process unit.

Device 20 may also be used for assessing the risk of hydrogen embrittlement in a workpiece that is receiving a treatment in a chemical bath such as a pickling treatment. The configuration of this device for this bath can be obtained from FIG. 14, where the electric device comprising items 82,83,84',84" is omitted.

Probe 21 is preferably a disposable probe, since, during the treatment and the measurement, it is coated with the specific coating of galvanic treatment bath 81, therefore device 20 is preferably made so as to assist replacing probe 21, i.e. to withdraw and position the latter from/into tank 80.

The foregoing description of specific exemplary embodiments of the device according to the invention, for application of a device for measuring hydrogen permeation, and of its mode of use, will so fully reveal the invention according to the conceptual point of view, such that others, by applying stream knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realise the different functions described herein could have a different nature without, for this reason, departing from the field of the invention. It is to be understood that the phraseology or terminology that is employed herein is for the purpose of description and not of limitation.

The invention claimed is:

1. A method for measuring a content of hydrogen absorbed by permeation in a workpiece in the form of hydrogen atoms, in order to characterize an interaction between said workpiece and said content of absorbed hydrogen that can weaken said workpiece or cause an embrittlement of said workpiece, comprising:
   providing a probe comprising:
   a collection element configured for being associated with said workpiece, wherein said collection element of said probe comprises an access opening for receiving an amount of absorbed hydrogen emanating from said workpiece;
   an inlet port for a measurement gas comprising air; and
   a mixing chamber arranged to pneumatically communicate with said inlet port, and with said collection element configured for mixing said measurement gas with said amount of hydrogen emanating from said workpiece, such that a gaseous mixture is formed in which said amount of emanating hydrogen is changed from said atomic form into a molecular form;
   providing a solid-state sensor in an inner portion of said probe, in such a way that said probe and said solid state sensor form a compact device;
   arranging said probe with said access opening facing said workpiece, such that an amount of hydrogen emanating from said workpiece passes through said access opening and enters into said mixing chamber;
   creating a flow of said air from said inlet port through said mixing chamber towards said solid-state sensor, at a predetermined flowrate, wherein said flow forms in said mixing chamber a gaseous mixture of said air with an amount of atomic hydrogen, emanating from said workpiece into a molecular form, and causes said gaseous mixture to contact said solid-state sensor;
   measuring a hydrogen concentration in said gaseous mixture by said solid-state sensor which is pneumatically connected with said mixing chamber so as to come into contact with said gaseous mixture in said mixing chamber, and generating by said solid-state sensor a measurement signal responsive to said hydrogen concentration of said gaseous mixture; and processing by a processor means connected to said solid-state sensor said measurement signal, said processor means comprising a program means which processes said measurement signal and calculates at least one parameter related to said interaction between said workpiece and said absorbed hydrogen.

2. The method according to claim 1, wherein said step of arranging said probe with said access opening facing said workpiece provides fastening said probe with said access opening in contact with said workpiece.

3. The method according to claim 1, wherein said step of providing a probe comprises providing a spacer duct that has a first end connected to said access opening and a second end, opposite to said first end, which is pneumatically connected with said mixing chamber.

4. The method according to claim 1, wherein an apparatus is provided which performs permeation tests in said workpiece, by a hydrogen gas source in said apparatus which generates a measurement hydrogen gas on a first face of said workpiece opposite to a second face of said workpiece, where said collection element is arranged;
wherein said processor means calculates an interaction parameter selected from the group consisting of:
a hydrogen diffusion coefficient or diffusivity in said workpiece;
an average content of hydrogen absorbed in said workpiece; and
a hydrogen distribution absorbed in said workpiece.

5. The method according to claim 4, wherein said hydrogen gas source in said apparatus is an electrolytic cell comprising:
an anode and a cathode brought to a voltage, and
an electrolytic solution arranged between said anode and said cathode,
wherein said cathode is set at a voltage equal to the voltage of said workpiece, and said electrolytic cell keeps said electrolytic solution in contact with said first face of said workpiece, and
wherein said voltage and said electrolytic solution are selected so as to cause a reduction reaction of said measurement hydrogen gas on said first face.

6. The method according to claim 1, wherein a step is provided to assess the risks of hydrogen embrittlement of a metal wall of a container used for containing a hydrogen-comprising gas or a fluid that can give rise to hydrogen, said step comprising the comparison of a hydrogen content C, determined according to claim 1, with a predetermined embrittlement content value C*, above which a significant risk arises of hydrogen embrittlement of said wall.

* * * * *